United States Patent
Suenaga et al.

(10) Patent No.: US 9,688,963 B2
(45) Date of Patent: Jun. 27, 2017

(54) CELL RELEASE METHOD

(71) Applicant: TOYO SEIKAN GROUP HOLDINGS, LTD., Tokyo (JP)

(72) Inventors: Ryo Suenaga, Kanagawa (JP); Takahiko Totani, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 0 days.

(21) Appl. No.: 14/981,447

(22) Filed: Dec. 28, 2015

(65) Prior Publication Data

US 2016/0208219 A1    Jul. 21, 2016

Related U.S. Application Data

(63) Continuation of application No. PCT/JP2014/002879, filed on May 30, 2014.

(30) Foreign Application Priority Data

Jun. 28, 2013 (JP) .................................. 2013-135912

(51) Int. Cl.
 C12M 1/00    (2006.01)
 C12N 5/074    (2010.01)
 C12M 1/26    (2006.01)
 C12N 5/0775    (2010.01)

(52) U.S. Cl.
 CPC ............ C12N 5/0696 (2013.01); C12M 33/12 (2013.01); C12M 33/18 (2013.01); C12N 5/0662 (2013.01); C12N 2509/10 (2013.01)

(58) Field of Classification Search
 CPC .................................................... C12M 33/12
 See application file for complete search history.

(56) References Cited

U.S. PATENT DOCUMENTS

| | | |
|---|---|---|
| 2007/0292946 A1 | 12/2007 | Nihei et al. |
| 2010/0178694 A1 | 7/2010 | Imaizumi et al. |
| 2010/0248367 A1 | 9/2010 | Kim |
| | (Continued) | |

FOREIGN PATENT DOCUMENTS

| | | |
|---|---|---|
| EP | 2141225 A1 | 1/2010 |
| EP | 2407533 A1 | 1/2012 |
| JP | H06-98756 A | 4/1994 |
| | (Continued) | |

OTHER PUBLICATIONS

Extended European Search Report issued in corresponding European Application No. 14818143.1 dated Jan. 4, 2017 (7 pages).

(Continued)

Primary Examiner — Rosanne Kosson
(74) Attorney, Agent, or Firm — Osha Liang LLP

(57) ABSTRACT

Adhesive culture cells cultured by using a culture container made of a flexible film can selectively be released from the culture container without causing damage to the cells. A cell release method for releasing, from a culture container, adhesive culture cells cultured adhering to the culture container made of a flexible film includes bringing a surface of the film of the culture container into contact with the adhesive culture cells, applying a pressure to the adhesive culture cells, and releasing the adhesive culture cells from the culture container, wherein the surface of the film faces a surface of the film of the culture container to which the adhesive culture cells adhere.

6 Claims, 8 Drawing Sheets

(56) References Cited

U.S. PATENT DOCUMENTS

2013/0230914  A1    9/2013  Totani et al.

FOREIGN PATENT DOCUMENTS

| | | |
|---|---|---|
| JP | 2531969 Y2 | 4/1997 |
| JP | 2008-000008 A | 1/2008 |
| JP | 2009-027944 A | 2/2009 |
| JP | 2011-115080 A | 6/2011 |
| JP | 2012-080836 A | 4/2012 |
| JP | 2012239401 A | 12/2012 |
| KR | 2010-0108497 A | 10/2010 |
| KR | 2011-0137300 A | 12/2011 |
| WO | 2009104296 A1 | 8/2009 |
| WO | 2010/076795 A1 | 7/2010 |

OTHER PUBLICATIONS

Office Action in corresponding Korean Patent Application No. 2015-7035563, dated Feb. 23, 2017, with translation (7 pages).
International Search Report issued in corresponding International Application No. PCT/JP2014/002879 mailed Sep. 2, 2014, and English translation thereof (5 pages).
Written Opinion of the International Searching Authority mailed Sep. 2, 2014, in corresponding International Application No. PCT/JP2014/002879 (4 pages).
Tetsuya Miwa et al., "Seisui Atsuryoku ni yoru Baiyo Saibo no Fuchaku Kyodo", Abstracts of Symposium on Colloid and Surface Chemistry, 2006, vol. 59, p. 237, 1G03, entire text.
International Preliminary Report on Patentability issued in corresponding International Application No. PCT/JP2014/002879 mailed Dec. 29, 2015 (2 pages).

FIG.8

CELL RELEASE METHOD

TECHNICAL FIELD

The present invention relates to a method of releasing, from a culture container, adhesive culture cells cultured by using the culture container, and more particularly, it relates to a method of releasing, from a culture container, adhesive culture cells cultured by using a sealed culture container made of a flexible film.

BACKGROUND ART

In recent years, in fields of medicine production, gene therapy, regenerative medicine, immunotherapy and the like, it is required that cells, tissues, microorganisms or the like are efficiently cultured in large amounts under an artificial environment, and the cells are automatically cultured in large amounts by use of a culture bag having a gas permeability in a closed system.

Additionally, in recent years, there have rapidly been developed research and development of the regenerative medicine and the like in which iPS cells having a versatile differentiation potency, mesenchymal stem cells having a differentiation potency to cells belonging to mesenchymal series, or the like are particularly used. Most of the cells for use in such research and development are adhesive culture cells.

The adhesive culture cells are cells that proliferate adhering to a culture container, and hence, these cells are different from floating cells that proliferate in a floating state in a culture liquid in that it is necessary to release the cultured cells from the culture container. Consequently, the adhesive culture cells have heretofore been often cultured in an opened culture container such as a petri dish to enable a releasing operation.

However, culturing the cells in large amounts in the petri dish is complicated and requires a great deal of time and labor, and hence, to efficiently culture the cells in large amounts in future, it is desirable to carry out the cultivation by use of a closed culture bag.

Additionally, in culturing the adhesive culture cells, it is necessary to only culture the selected cells having an excellent condition or the like, and hence it is also required that a desirable portion is only released from the culture container.

As a conventional cell release method, a trypsin treatment can first be quoted. In this method, an adhesion factor of the adhesive culture cells to the culture container is decomposed with trypsin that is a proteolytic enzyme, whereby the cells are released.

Figure 8:
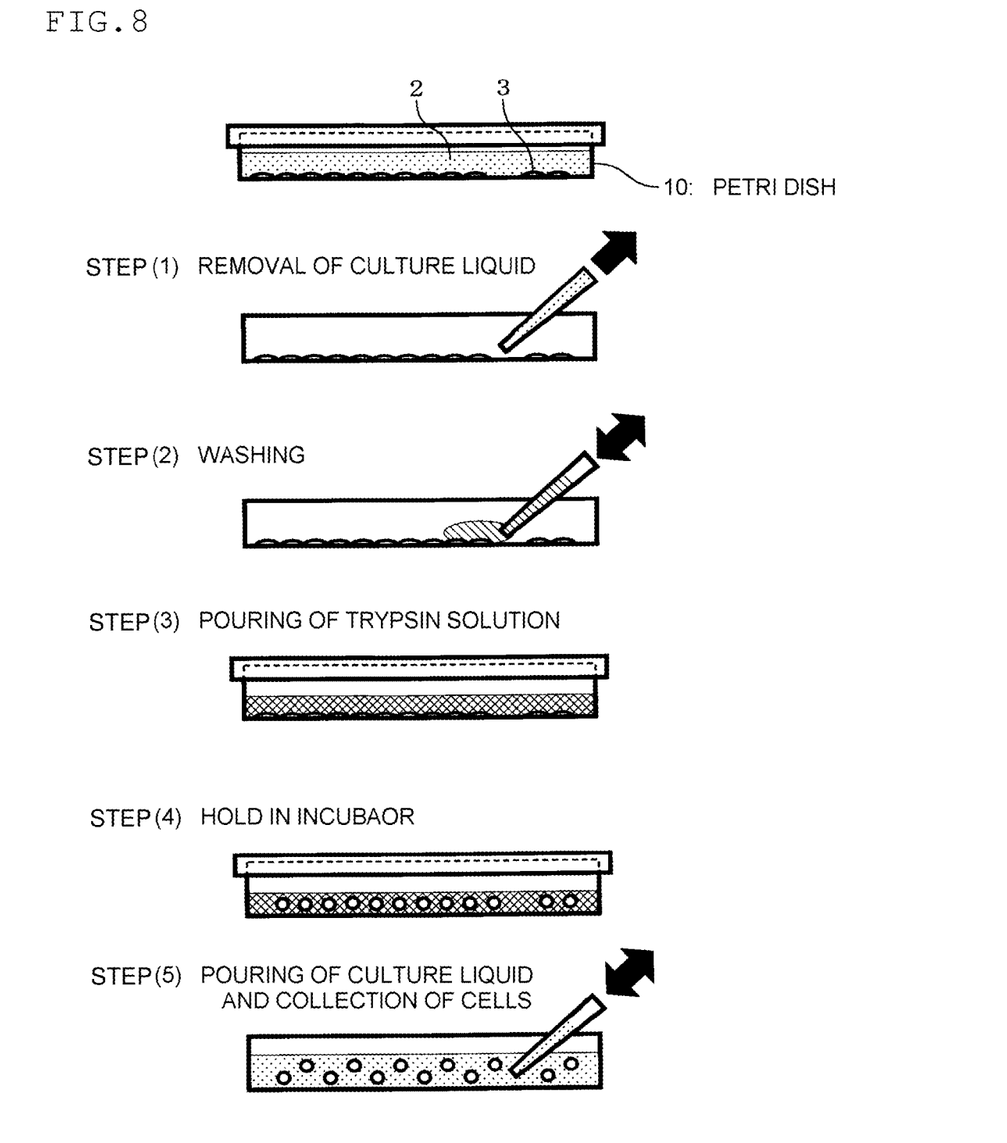
FIG. 8 shows a cell release method by a conventional trypsin treatment.

That is, as shown in FIG. 8, a petri dish 10 into which a culture liquid 2 is placed is seeded with adhesive culture cells 3 to proliferate the cells, and then the culture liquid 2 is removed from the petri dish 10 shown in step (1) of FIG. 8. Next, culture liquid components are washed with phosphate buffered saline (a PBS solution) shown in step (2) of FIG. 8, and a trypsin solution is poured thereinto shown in step (3) of FIG. 8. The solution is held in an incubator for several minutes to decompose the adhesion factor, and the adhesive culture cells 3 are released in pieces from the petri dish 10 shown in step (4) of FIG. 8. Finally, the culture liquid 2 is poured into the petri dish 10 to devitalize trypsin, and the adhesive culture cells 3 are collected together with the culture liquid 2 shown in step (5) of FIG. 8.

According to such a trypsin treatment, the adhesive culture cells 3 can be released from the culture container.

In addition, as a conventional cell release method, there is also a method which physically scrapes cells by use of a cell scraper (see Patent Document 1). According to this method, an operation is easier than in the trypsin treatment, and cells in a targeted range can be released to a certain degree.

Furthermore, Patent Document 2 discloses a method in which a scanning type probe microscope having a probe is utilized and the probe is pressed onto specific cells with a predetermined force to apply a physical stimulus to the cells, thereby releasing the cells from a substrate. According to this method, the cells can selectively be released.

Patent Document 1: Japanese Utility Model Registration No. 2531969

Patent Document 2: Japanese Patent No. 4831543

SUMMARY OF THE INVENTION

However, in a trypsin treatment, when a holding time in an incubator is excessively long, even cell membranes are decomposed, and cells might be damaged. In addition, an operation is complicate, and it is difficult to apply the treatment to a culture bag. Furthermore, it is difficult to only release part of cell groups, and hence a desire to only release a desirable portion is not satisfied.

In addition, a method in which a cell scraper is used as described in Patent Document 1 is suitable for an opened culture container having a large opening, and it is difficult to apply this method to a culture bag having a small opening.

Additionally, in a method in which a scanning type probe microscope having a probe is utilized as described in Patent Document 2, the probe is used, and hence it is difficult to apply the method to the culture bag. In addition, cells are selectively released one by one, and hence adhesive culture cells cultured in large amounts in the culture bag cannot efficiently be released.

Consequently, there has been required a technology capable of selectively and efficiently releasing, from the culture bag, the adhesive culture cells cultured by using the culture bag.

The present inventors have intensively studied a cell release method which can be applied to the culture bag. Further, it has been found that a surface of a film facing a surface of the film of the culture bag to which the adhesive culture cells adhere is brought into contact with the adhesive culture cells and a pressure is applied to the adhesive culture cells, whereby the adhesive culture cells can be released from the inner surface of the culture bag.

A cell release method according to one or more embodiments is capable of selectively and efficiently releasing, from a culture container, adhesive culture cells cultured by using the culture container made of a flexible film without causing damage to the cells.

The cell release method according to one or more embodiments of the present invention releases, from a culture container, adhesive culture cells cultured adhering to the culture container made of a flexible film, the method comprising bringing a surface of the film of the culture container facing a surface of the film of the culture container to which the adhesive culture cells adhere, into contact with the adhesive culture cells, and applying a pressure to the adhesive culture cells, thereby releasing the adhesive culture cells from the culture container.

According to one or more embodiments of the present invention, it is possible to provide a cell release method which easily, selectively and efficiently releases, from a culture container, adhesive culture cells cultured by using the culture container made of a flexible film without causing damage to the cells.

BRIEF DESCRIPTION OF THE DRAWINGS

In each figure, capital letters in the English alphabet (e.g., (A), (B), (C)) indicate subfigures. On the other hand, the Arabic numerals in parentheses (e.g., (1), (2), (3)) indicate steps.

DETAILED DESCRIPTION OF THE INVENTION

The cell release method according to one or more embodiments of the present invention releases, from a culture container, adhesive culture cells cultured adhering to the culture container made of a flexible film, and may be a method of bringing a surface of the film of the culture container facing a surface of the film of the culture container to which the adhesive culture cells adhere, into contact with the adhesive culture cells, and applying a pressure to the adhesive culture cells, thereby releasing the adhesive culture cells from the culture container, and the method is not especially limited to another constitution.

That is, according to one or more embodiments, there is not any special restriction on means for applying the pressure to the adhesive culture cells, as long as the surface of the film of the culture container facing the surface of the film of the culture container to which the adhesive culture cells adhere can be brought into contact with the adhesive culture cells and the pressure can be applied to the adhesive culture cells, and the pressure may be applied to the cells from the outside of the culture container, or air in the culture container may be adjusted into a negative pressure to apply the pressure to the cells.

In addition, as a method of applying the pressure from the outside of the culture container, the culture container may be pressed with a pressing member or the like, or the culture container may be pressed with an air pressure or the like.

Hereinafter, embodiments of the present invention will specifically be described.

First Example

First, embodiments of the cell release method of the first example of the present invention will be described in detail with reference to FIG. 1 and FIG. 2.

Figure 1:
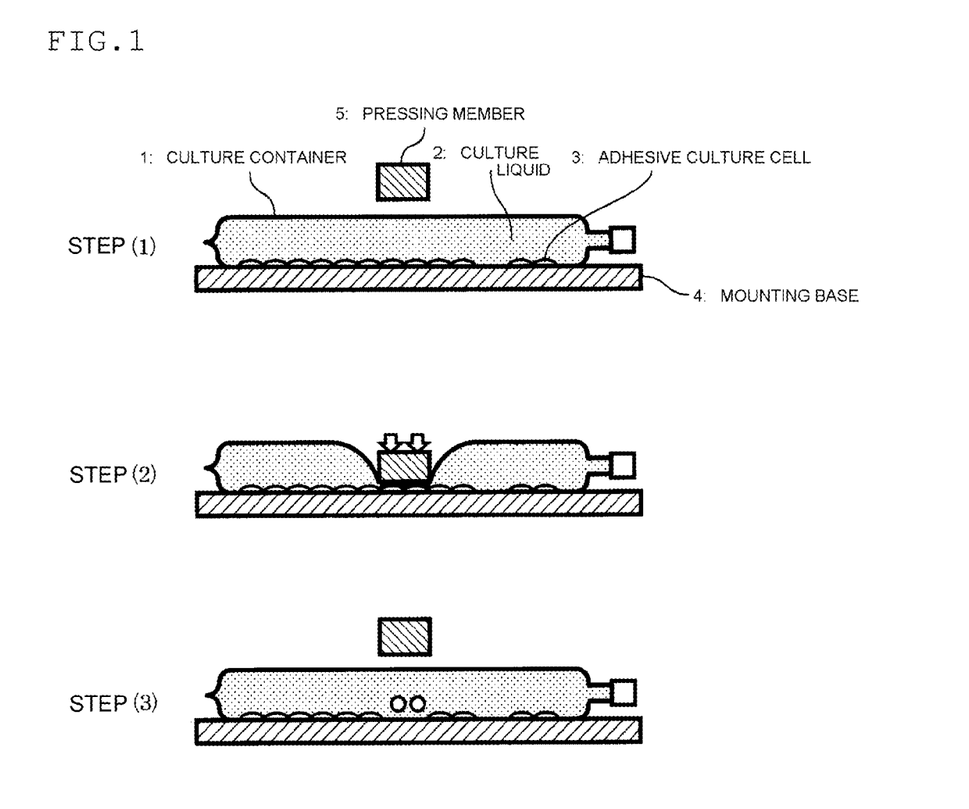
FIG. 1 shows steps of one or more embodiments of the cell release method of the first example of the present invention.

Step (1) of FIG. 1 schematically shows a behavior that a culture liquid 2 and adhesive culture cells 3 are enclosed in a culture container 1 made of a flexible film (a culture bag) and mounted on a mounting base 4, and a pressing member 5 is disposed above the culture container 1. The adhesive culture cells 3 are cultured adhering to a bottom surface of the film in the culture container 1.

Next, as shown in step (2) of FIG. 1, the culture container 1 is pressed from the upside with the pressing member 5. At this time, an upper surface of the film in the culture container 1 is brought into contact with the adhesive culture cells 3, and a pressure is applied to the adhesive culture cells 3 to such an extent that the adhesive culture cells 3 are not damaged.

Further, as shown in step (3) of FIG. 1, when the pressing member 5 is detached from the culture container 1, the adhesive culture cells 3 are released from the bottom surface of the film in the culture container 1.

Here, even when the adhesive culture cells 3 adhering to the bottom surface of the film in the culture container 1 are rubbed from the downside of the culture container 1, the cells cannot be released. That is, even when the force is applied from the outside of the culture container 1 to the surface of the film of the culture container 1 to which the adhesive culture cells adhere, the film is only scratched or stretched, and the adhesive culture cells 3 cannot be released.

On the other hand, according to one or more embodiments of the abovementioned cell release method, the adhesive culture cells 3 adhering to the inside of the culture bag can selectively and efficiently be released without being damaged, to a certain degree in a targeted range.

The reason is not clarified, but it is presumed that when the film of the culture container 1 is brought into contact with the adhesive culture cells 3 and the pressure is applied to the cells as in one or more embodiments of the present invention, stress larger than an adhesive force of the adhesive culture cells 3 to the culture container 1 acts on the adhesive culture cells, to separate the adhesive culture cells 3 from the culture container 1.

The culture container 1 is the culture bag made of the flexible film obtained by shaping a soft packaging material in the form of the bag. The culture container 1 is for use in culturing the adhesive culture cells 3, and therefore has a gas permeability, and a part or all of the culture container may have transparency so that contents can be confirmed. Examples of the material of the film satisfying such conditions include polyolefin, ethylene-vinyl acetate copolymer, styrene elastomer, polyester thermoplastic elastomer, silicone thermoplastic elastomer, and silicone rubber.

In addition, for the purpose that the adhesive culture cells 3 can adhere to the inside of the culture container 1, it is necessary to adjust the inside of the culture container 1 into a hydrophilic state, or it is necessary to coat the inside of the culture container with a sufficient amount of adhesion factor such as fibronectin. An example of a method of adjusting the inside of the culture container 1 into the hydrophilic state is a method of forming the culture container 1 by use of a film subjected to a UV ozone treatment or a corona treatment. An example of a method of coating the inside of the culture container with the adhesion factor is a method of impregnating the inside of the culture container 1 with a solution of the adhesion factor and holding the container for a predetermined time to adsorb the adhesion factor by an inner surface of the culture container 1.

Furthermore, the culture container 1 comprises one or two or more ports through which the culture liquid 2 and the adhesive culture cells 3 are inserted and removed.

There is not any special restriction on the culture liquid 2 as long as the adhesive culture cells 3 can be cultured, and the existing liquid is usable. For example, a culture liquid obtained by adding 10% of FBS (fetal brovine serum) to DMEM (Dulbecco Vogt modified Eagle's minimal essential medium) or the like is suitably usable.

There is not any special restriction on the adhesive culture cells 3 as long as the cells proliferate adhering to the inside of the culture container 1. However, for example, iPS cells, mesenchymal stem cells or the like are usable.

The mounting base 4 is a flat base on whose upper surface the culture container 1 is mounted. In the mounting base 4, there can be disposed, for example, a fixing tool to fix the culture container 1 to the mounting base 4, and various configurations to stationarily dispose the culture container 1.

The pressing member 5 is a member which presses the culture container 1 from the outside of the culture container 1 to bring the surface of the film of the culture container 1 facing the surface of the film of the culture container 1 to which the adhesive culture cells 3 adhere, into contact with the adhesive culture cells 3, and applies the pressure to the adhesive culture cells 3.

Figure 2A:
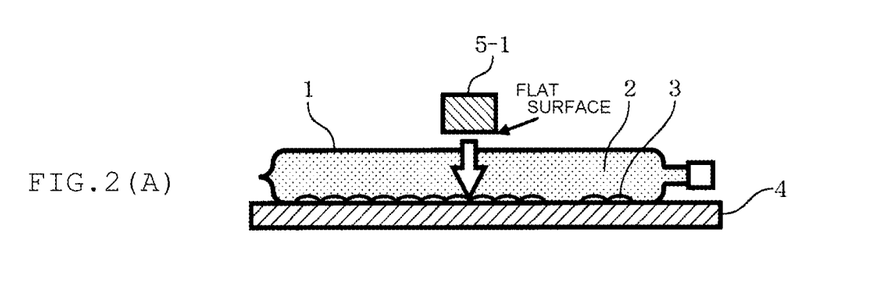
FIGS. 2(A)-2(C) are views showing embodiments of a pressing member of the cell release method of the first example of the present invention.

As the pressing member 5, a member having a three-dimensional shape whose bottom surface is a flat surface is usable as shown in, for example, FIG. 2(A). When such a pressing member 5-1 whose bottom surface is the flat surface is used, it is possible to selectively and efficiently release the adhesive culture cells 3 adhering to the film in a definite region of the culture container 1 pressed by the flat surface. Examples of such a three-dimensional shape include a rectangular parallelepiped, a cube, a column, a cone, and a polygonal prism.

Figure 2B:
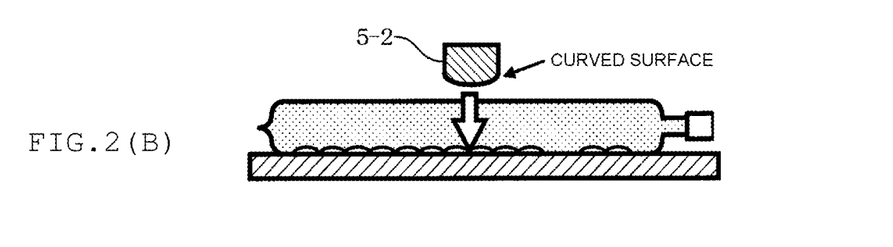

In addition, as the pressing member 5, a member having a three-dimensional shape whose bottom surface is a curved surface (a convex surface projected downward) is usable as shown in, for example, FIG. 2(B). When such a pressing member 5-2 whose bottom surface is the curved surface is used, it is possible to selectively release the adhesive culture cells 3 adhering to the film in a narrower definite region of the culture container 1.

Figure 2C:
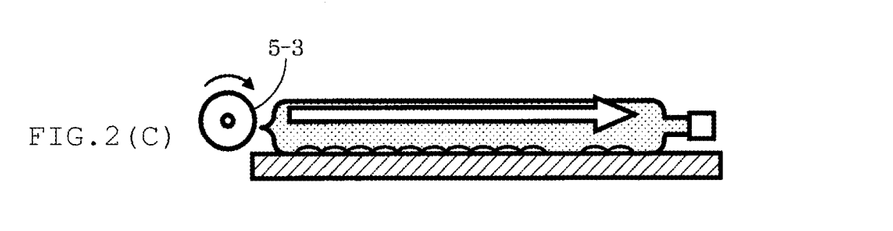

Furthermore, as the pressing member 5, for example, a roller 5-3 is usable as shown in FIG. 2(C). That is, the culture container 1 is pressed with the roller from the upside, the surface of the film of the culture container 1 facing the surface of the film of the culture container 1 to which the adhesive culture cells 3 adhere is brought into contact with the adhesive culture cells 3, and the roller 5-3 is moved in parallel with the mounting base 4 while applying the pressure to the adhesive culture cells 3. In consequence, it is possible to selectively and efficiently release the adhesive culture cells 3 adhering to the film in a broader definite region of the culture container 1. In particular, using the roller 5-3 as the pressing member 5 is suitable in efficiently releasing all the adhesive culture cells 3 in the culture container 1.

Second Example

Next, embodiments of the cell release method of the second example of the present invention will be described with reference to FIG. 3. In one or more embodiments, as a mounting base 4, a base comprising a hole 4-1 is used, and hence adhesive culture cells 3 as release objects are easier to be selected. The other respects are similar to the first embodiment, and a culture container 1, a culture liquid 2, adhesive culture cells 3 and a pressing member 5 similar to those of the first embodiment are usable.

Figure 3:
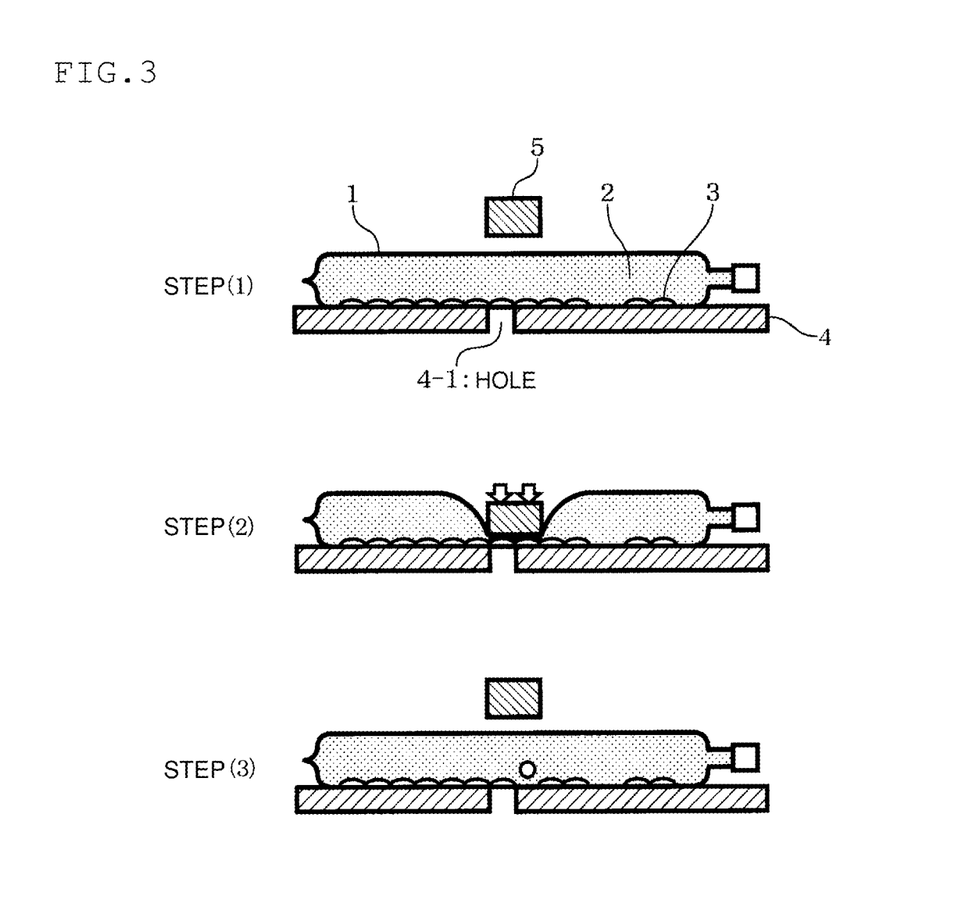
FIG. 3 shows steps of one or more embodiments of the cell release method of the second example of the present invention.

That is, in one or more embodiments of the cell release method, as shown in FIG. 3, the mounting base in which the hole 4-1 is formed in its definite region is used as the mounting base 4, and among the adhesive culture cells 3 cultured adhering to an inner surface of the culture container 1, a definite region of the culture container 1 to which the adhesive culture cells 3 which are not to be released adhere is disposed above the hole 4-1. Further, a range including the region is pressed with the pressing member 5 from the outside of the culture container 1, and without releasing the adhesive culture cells 3 adhering to the region, the adhesive culture cells 3 only adhering to the pressed range other than the region can selectively be released.

Specifically, step (1) of FIG. 3 schematically shows a behavior that the culture liquid 2 and the adhesive culture cells 3 are enclosed in the sealed culture container 1 made of a flexible film (a culture bag) to be mounted on the mounting base 4 comprising the hole 4-1, and the pressing member 5 is disposed above the culture container 1. The adhesive culture cells 3 are cultured adhering to a bottom surface of the film in the culture container 1.

Next, as shown in step (2) of FIG. 3, the culture container 1 is pressed with the pressing member 5 from the upside of the range including the hole 4-1. At this time, an upper surface of the film in the culture container 1 comes in contact with the adhesive culture cells 3, and a pressure is applied to the adhesive culture cells 3 adhering to the region other than a region above the hole 4-1 to such an extent that the adhesive culture cells 3 are not damaged. On the other hand, the adhesive culture cells 3 adhering to the region above the hole 4-1 are sunk into the hole 4-1 when pressed from the upside, and a pressure required to release the cells is not applied to the adhesive culture cells 3.

As a result, as shown in step (3) of FIG. 3, when the pressing member 5 is detached from the culture container 1, the adhesive culture cells 3 adhering to the region other than the region above the hole 4-1 are only released from the bottom surface of the film in the culture container 1, and the adhesive culture cells 3 adhering to the region above the hole 4-1 are not released from the bottom surface of the film in the culture container 1.

Thus, according to one or more embodiments of the cell release method, the culture container 1 is disposed on the mounting base 4 so that the adhesive culture cells 3 which are not to be released are positioned above the hole 4-1 of the mounting base 4, and hence it is possible to more finely select the adhesive culture cells 3 to be released.

It is to be noted that FIG. 3 shows the hole 4-1 as a hole formed to extend through the mounting base 4, but the present invention is not limited to this example, and the hole may be formed as a dent in the mounting base 4. In addition, a shape of the hole in a horizontal surface of the mounting base 4 may be optional, and the hole may be formed into a free shape comprising a curved line or the like in addition to a round shape, a rectangular shape, a polygonal shape or the like. Furthermore, the number of the holes is not limited to one, and two or more holes 4-1 may be disposed in the mounting base 4.

Additionally, in one or more embodiments, the range including the region disposed above the hole 4-1 can be pressed by, for example, an air pressure, a liquid pressure or the like without using the pressing member 5.

Third Example

Next, embodiments of the cell release method of the third example of the present invention will be described with reference to FIG. 4. In one or more embodiments of the cell release method, the inside of a culture container 1 is adjusted into a negative pressure, thereby bringing a surface of a film of the culture container 1 facing a surface of the film of the culture container 1 to which adhesive culture cells 3 adhere, into contact with the adhesive culture cells 3 and applying a pressure to the adhesive culture cells 3. The culture container 1, a culture liquid 2, the adhesive culture cells 3 and a mounting base 4 similar to those of the first embodiment are usable.

That is, in one or more embodiments of the cell release method, the culture liquid 2 is discharged from the culture container 1, and next air of the culture container 1 is sucked to adjust the inside of the culture container 1 into the negative pressure, thereby bringing the surface of the film of the culture container 1 facing the surface of the film of the culture container 1 to which the adhesive culture cells 3 adhere, into contact with the adhesive culture cells 3 and applying the pressure to the adhesive culture cells 3. Next, the culture liquid 2 is poured into the culture container 1 to release the adhesive culture cells 3 from an inner surface of the culture container 1.

Figure 4:
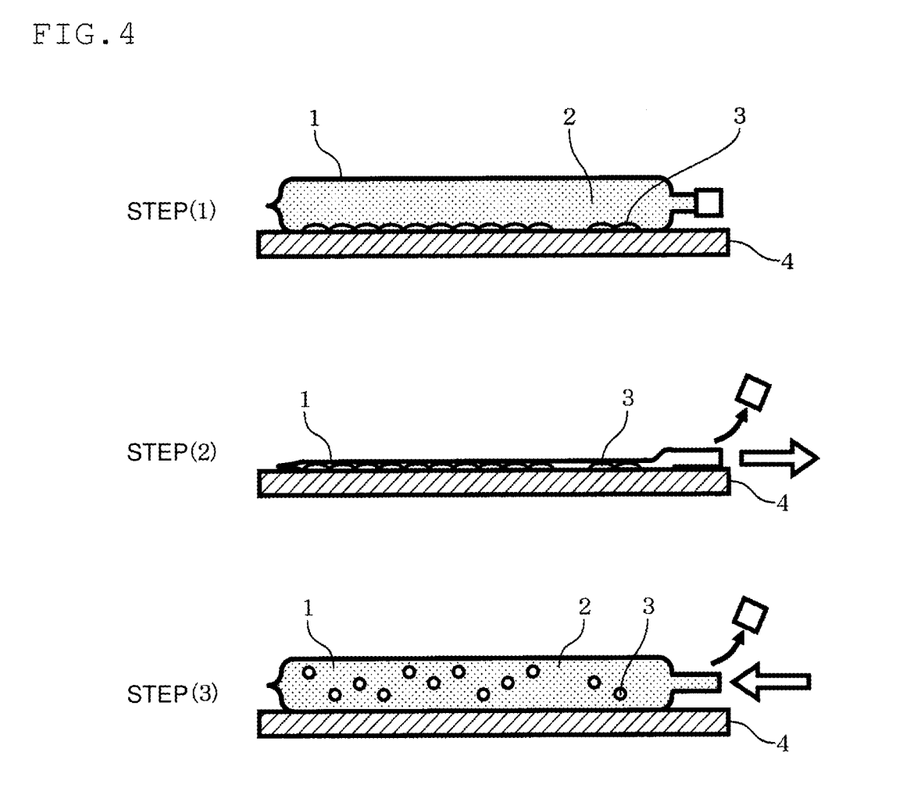
FIG. 4 shows steps of one or more embodiments of the cell release method of the third example of the present invention.

Specifically, step (1) of FIG. 4 schematically shows a behavior that the culture liquid 2 and the adhesive culture cells 3 are enclosed in the sealed culture container 1 (a culture bag) made of a flexible film to be mounted on the mounting base 4. The adhesive culture cells 3 are cultured adhering to a bottom surface of the film in the culture container 1.

Next, as shown in step (2) of FIG. 4, the culture liquid 2 is discharged from the culture container 1 and further, air in the culture container 1 is sucked with a pump or the like, to adjust the inside of the culture container 1 into the negative pressure. In consequence, the surface of the film of the culture container 1 facing the surface of the film of the culture container 1 to which the adhesive culture cells 3 adhere is brought into contact with the adhesive culture cells 3 and the pressure is applied to the adhesive culture cells 3.

Furthermore, as shown in step (3) of FIG. 4, the culture liquid 2 is poured into the culture container 1, thereby releasing the adhesive culture cells 3 from the inner surface of the culture container 1.

According to one or more embodiments of the cell release method, the adhesive culture cells 3 in the culture container 1 can easily and efficiently be released without causing damage to the cells.

EXAMPLES

Example 1

An experiment was carried out in which adhesive culture cells 3 were released from a culture bag 1 by a cell release method of the above first embodiment.

In the culture bag 1, a bag made of polyethylene (PE) and having a size of 100 mm×225 mm and a film thickness of 0.1 mm was used. The inside of the culture bag 1 was coated with fibronectin.

Specifically, in a state where an inner surface of the culture bag 1 was entirely impregnated with 100 ml of a fibronectin solution diluted in 5 μg/ml with PBS (a phosphate buffered saline solution), the culture bag was held at 37° C. in a $CO_2$ incubator for about 2 hours.

Next, the total amount of the fibronectin solution was discharged, and then the inner surface of the culture container 1 was washed with PBS once (immediately after the whole inner surface of the culture bag was impregnated with 100 ml of PBS, the solution was discharged). The liquid was supplied and discharged by connecting a syringe to a port disposed in the culture bag 1.

As the adhesive culture cells 3, CHO (Chinese hamster ovary) cells were used. Additionally, as a culture liquid 2, a DMEM medium containing 10% of FBS (fetal brovine serum) was used. The culture bag 1 was seeded with these 2,000,000 CHO cells together with 150 ml of culture liquid, and the cells statically cultured for 72 hours were used to carry out a releasing experiment.

The culturing was carried out in a $CO_2$ incubator at 37° C., a $CO_2$ concentration of 5% and a humidity of 97% which were conditions.

Figure 5A:
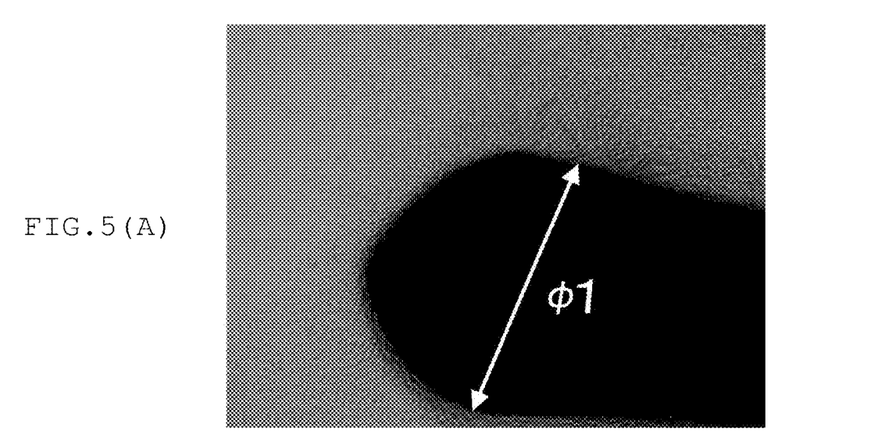
FIGS. 5(A) and 5(B) are views showing microscope photographs of the result of Example 1.
Figure 5B:
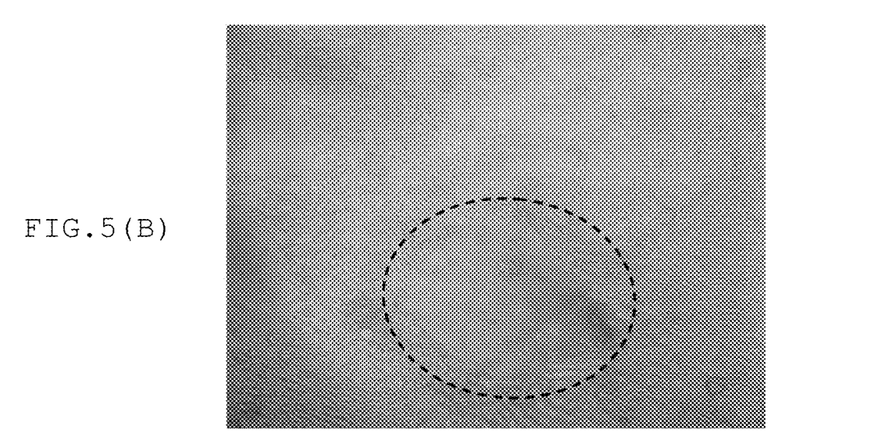

In the releasing experiment, as a pressing member 5, a pin having a round tip and a thickness of 1 mm (the tip of SRI) was used, and as a mounting base 4, a glass plate was used. Further, this pin was picked with a finger and lightly pressed onto a culture bag. At this time, a pressure was several tens of gf, and the pin was pressed downward until stress from the glass plate was felt. Further, the pin was detached from the culture bag 1. FIG. 5 shows the result.

FIG. 5(A) shows a microscope photograph of a state where the culture bag 1 is pressed with the pin, and FIG. 5(B) shows a microscope photograph of a state where the pin is detached from the culture bag 1. From FIG. 5(B), it is seen that the adhesive culture cells 3 are released only in a region of the culture bag 1 pressed with the pin.

Therefore, it has been clarified that, according to the cell release method of the first embodiment, the adhesive culture cells adhering to the inside of the culture bag can selectively and efficiently be released.

Example 2

Figure 6A:
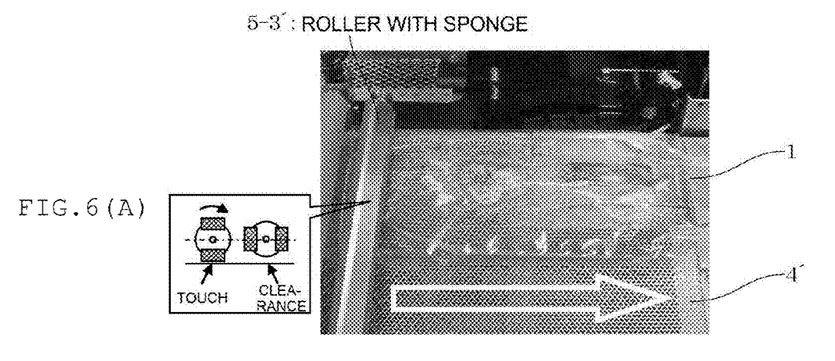
FIGS. 6(A)-6(D) are views showing microscope photographs and the like of a behavior and result of Example 2.

An experiment was carried out in which adhesive culture cells 3 were released from a culture bag 1 by a cell release method of the above second embodiment. The same culture container 1, culture liquid 2 and adhesive culture cells 3 as in Example 1 were used. In the present example, the culture bag 1 was mounted on a mounting base 4' comprising a hole 4-1, and a roller 5-3' was rotated and moved in parallel with the mounting base 4' while pressing the culture bag 1 with the roller 5-3'. As the roller 5-3', there was used a roller capable of pressing down the culture bag 1 every definite interval as mentioned below.

Specifically, as shown in FIG. 6(A), the roller 5-3' with sponges was used as a pressing member 5. In the roller 5-3' with the sponges, two elongated plate-like sponges were attached to a roller entirely in a longitudinal direction to face a part of the roller on a circumferential surface of the roller. Each of these sponges was a silicon sponge having Asker C15 hardness, and there were used the sponges each having a width of 6.5 mm, a thickness of 3 mm and the same length as that of the roller in the longitudinal direction.

While the roller 5-3' with such sponges rotates and moves on the culture bag 1, the culture bag 1 can be pressed when the sponges are positioned downward, and the culture bag 1 is not pressed when the sponges are positioned upward or in a lateral direction. When the roller 5-3' with the sponges are used, rotated and moved while pressing the roller onto the culture bag 1, a portion pressed by the roller 5-3' with the sponges and a portion which is not pressed by the roller are generated in the culture bag 1.

Figure 6B:
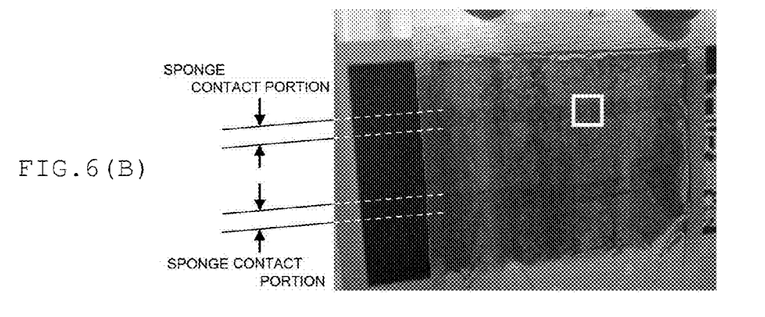
Figure 6C:
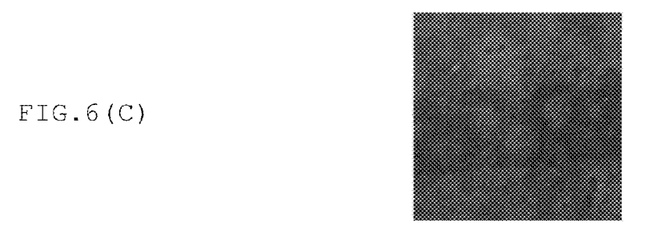
Figure 6D:
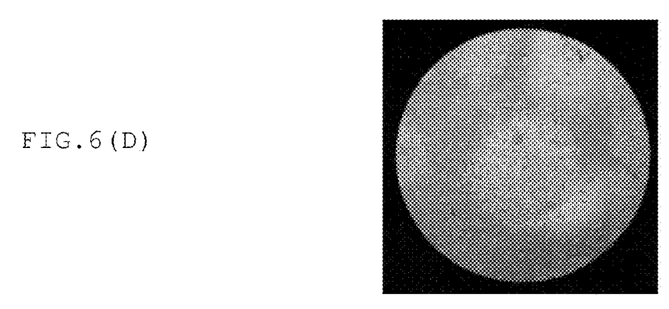

In addition, as the mounting base 4', a punching metal plate made of stainless steel (a hole diameter of 2 and a porosity of 40.2) was used. The mounting base 4' comprised a large number of holes. In the present example, there were only selectively released the adhesive culture cells 3 adhering to a region which was pressed by the roller 5-3' with the sponges and was not above the hole of the mounting base 4' in the culture container 1 mounted on the mounting base 4'. FIGS. 6(B) to (D) show the result.

That is, FIG. 6(B) shows a behavior that regions which come in contact with the sponges are only black and the other region to which the cells adhere appears to be white in the culture bag 1. FIG. 6(C) is a photograph in which a part surrounded with a white line in FIG. 6(B) is enlarged, and it is seen that cells in white adhere to a region corresponding to the hole of the mounting base 4'. FIG. 6(D) is a microscope photograph including a periphery of the region corresponding to the hole of the mounting base 4', and it is seen that the adhesive culture cells 3 adhering to the region corresponding to the hole are not released and the adhesive culture cells 3 adhering to the periphery are only released.

Therefore, it has been clarified that, according to the cell release method of the second embodiment, the adhesive culture cells 3 adhering to the inside of the culture bag 1 can more finely selectively be released.

(Culturing Test)

For the purpose of confirming that the adhesive culture cells released by one or more embodiments of the cell release method can be cultured without being damaged, a culturing test was carried out to compare and confirm cultured states of cells cultured after scraped by using a conventional cell scraper and cells cultured after released by one or more embodiments of the cell release method.

(1) Culturing Test of Adhesive Culture Cells Scraped by Using Cell Scraper

As a culture container, Falcon tissue culturing dish (φ6 cm) was used, and as a culture liquid, 4 ml of DMEM medium containing 10% of FBS (fetal brovine serum) was used. In addition, CHO cells were used as adhesive culture cells, a seeding density was set to $1\times10^5$ cells/ml and a $CO_2$ incubator was used to carry out the culturing at 37° C., a $CO_2$ concentration of 5% and a humidity of 97% which were conditions. A subculture interval was set to 72 hours, and subculturing was carried out by a technique mentioned below.

First, the culture container was taken out from the $CO_2$ incubator, and supernatant was sucked out with a pipette to discharge a total amount of the supernatant. Next, the whole surface in the culture container was rubbed with a cell scraper, and the cells were scraped. Further, 2 ml of fresh culture liquid was poured into the culture container, and pipetting was performed to loosen the cells. The cells were collected in another container (a conical tube) once, and from the container, a remarkably small amount of the cells were sampled, to count the number of the cells by use of a blood corpuscle counting board. The culture liquid was poured to set a cell density to $1\times10^5$ cells/ml on the basis of the counted value. Further, a new culture container was seeded with 4 ml of the obtained cell suspension, and stored again in the incubator for 72 hours. This subculturing method was repeated to continue culturing for half a year or more.

(2) Culturing Test of Adhesive Culture Cells Released in Example 2

The adhesive culture cells released in Example 2 were collected in a conical tube to sample a remarkably small amount of the cells, and the number of the cells was counted by using a blood corpuscle counting board. A culture liquid (a DMEM medium containing 10% of FBS) was poured to set a cell density to $1\times10^5$ cells/ml on the basis of the counted value. Further, a new culture container was seeded with 4 ml of the obtained cell suspension, and stored in an incubator for 72 hours.

Figure 7A:
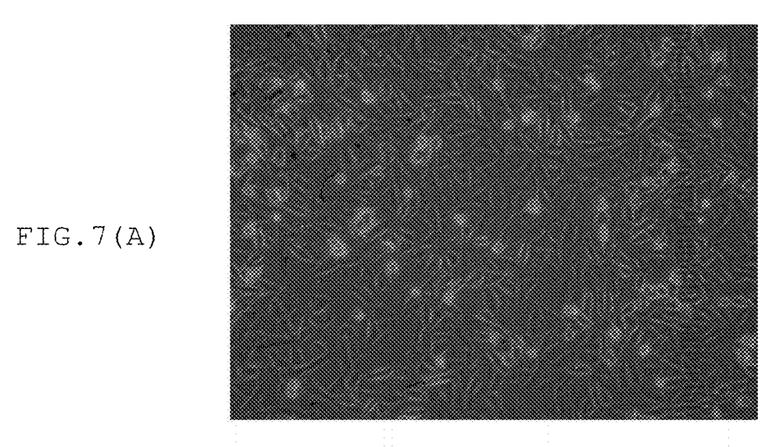
FIGS. 7(A) and 7(B) are views showing microscope photographs of the respective results of seeding with the same density and culturing of adhesive culture cells released to be subcultured by a conventional method and adhesive culture cells obtained as a result of Example 2.
Figure 7B:
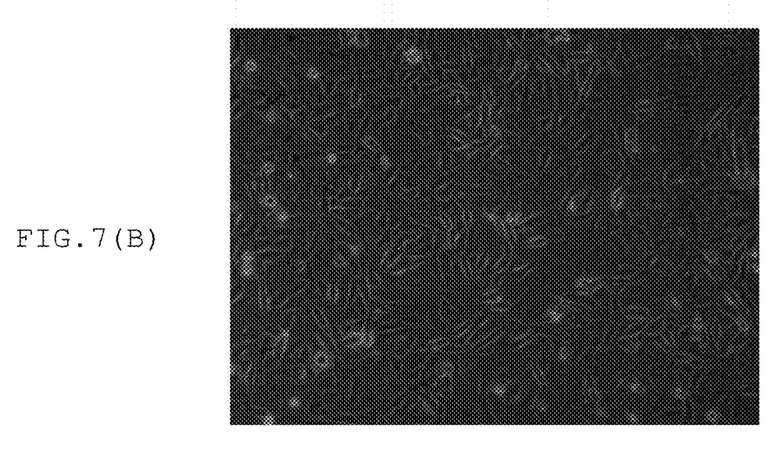

FIG. 7(A) is a microscope photograph of adhesive culture cells scraped by using a cell scraper and subcultured for half a year or more. Additionally, FIG. 7(B) is a microscope photograph of adhesive culture cells released in Example 2 and cultured for 72 hours by using the same seeding density and culturing conditions as in the adhesive culture cells scraped by using the cell scraper.

When these microscope photographs are compared, it is seen that about the same cell proliferating ratio and about the same adhesion ratio (the ratio at which elongated cells adhere) can be obtained.

Therefore, it has been clarified that the adhesive culture cells released by one or more embodiments of the cell release method of the present invention can be released without damaging any cells.

Needless to say, the present invention is not limited to the embodiments or examples mentioned above, and various change implementations are possible within the scope of the present invention.

For example, in place of using the pressing member, change can suitably be made so that, for example, about the same degree of air pressure or liquid pressure as in a case where the pressing member is used is applied to the adhesive culture cells from the outside of the culture container, thereby releasing the adhesive culture cells from the culture container.

INDUSTRIAL APPLICABILITY

One or more embodiments of the present invention can suitably be utilized in a case where adhesive culture cells are cultured in large amounts.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

DESCRIPTION OF REFERENCE NUMERALS 1 culture container
2 culture liquid
3 adhesive culture cell
4 mounting base
4' mounting base (a punching metal plate)
4-1 hole
5 pressing member
5-1 pressing member whose bottom surface is a flat surface
5-2 pressing member whose bottom surface is a curved surface
5-3 roller
5-3' roller with sponge
10 petri dish

The invention claimed is:

1. A cell release method for releasing, from a culture container made of a flexible film, adherent cells that adhere to the culture container during cell culture, the method comprising:
   a) bringing a first side of the culture container into contact with the adherent cells that have adhered to a second side of the culture container, by pressing on the exterior of the first side with a Dressing member, thereby applying pressure to a region below the pressing member, wherein the pressing releases the cells from the second side of the culture container, and
   b) removing the adherent cells from the culture container.

2. The cell release method according to claim 1, wherein the pressing member has a flat bottom surface.

3. The cell release method according to claim 1, wherein the pressing member has a curved bottom surface.

4. The cell release method according to claim 1, wherein the pressing member is a roller.

5. The cell release method according to claim 1, further comprising:
   a) disposing a region of the culture container to which the adherent cells which are not to be released have adhered above one or more holes of a mounting base on which the culture container is mounted,
   b) pressing a region of the culture container including the region disposed above the one or more holes, and selectively releasing the adherent cells in the pressed region without releasing the cells in the region above the holes.

6. The cell release method according to claim 1, wherein the first and second sides are brought into contact by removing culture medium and air from the culture container, thereby creating a negative pressure in the culture container, and wherein the released cells are removed by adding culture medium to the culture container and removing a suspension of the cells in the culture medium.

* * * * *

UNITED STATES PATENT AND TRADEMARK OFFICE
CERTIFICATE OF CORRECTION

| | | |
|---|---|---|
| PATENT NO. | : 9,688,963 B2 | Page 1 of 1 |
| APPLICATION NO. | : 14/981447 | |
| DATED | : June 27, 2017 | |
| INVENTOR(S) | : Ryo Suenaga et al. | |

It is certified that error appears in the above-identified patent and that said Letters Patent is hereby corrected as shown below:

On the Title Page

Item (56) References Cited, the following patent is missing from the list of U.S. PATENT DOCUMENTS, and should be added to read 8,093,051-B2-01/2012-Kim.

In the Claims

At Column 11, Claim number 1, Line number 9, "Dressing" should read -- pressing --

Signed and Sealed this
Third Day of October, 2017

Joseph Matal
*Performing the Functions and Duties of the
Under Secretary of Commerce for Intellectual Property and
Director of the United States Patent and Trademark Office*